United States Patent
Honda et al.

(10) Patent No.: US 6,449,337 B1
(45) Date of Patent: Sep. 10, 2002

(54) X-RAY COMPUTED TOMOGRAPHY APPARATUS

(75) Inventors: Toyomasa Honda; Wataru Taguchi, both of Nasu-gun (JP)

(73) Assignee: Kabushiki Kaisha Toshiba, Kawasaki (JP)

(\*) Notice: Subject to any disclaimer, the term of this patent is extended or adjusted under 35 U.S.C. 154(b) by 0 days.

(21) Appl. No.: 09/654,051

(22) Filed: Sep. 1, 2000

(30) Foreign Application Priority Data

Nov. 24, 1999 (JP) .......................... 11-333370

(51) Int. Cl.⁷ .............................. H05G 1/54
(52) U.S. Cl. ................. 378/117; 378/118; 378/901
(58) Field of Search .............. 378/117, 118, 378/901

(56) References Cited

U.S. PATENT DOCUMENTS 4,649,555 A \* 3/1987 Matsubayashi ............... 378/4
5,566,218 A \* 10/1996 Nobuta et al. .............. 378/117

\* cited by examiner

*Primary Examiner*—Robert H. Kim
*Assistant Examiner*—Chih-Cheng Glen Kao
(74) *Attorney, Agent, or Firm*—Oblon, Spivak, McClelland, Maier & Neustadt, P.C.

(57) ABSTRACT

An X-ray computed tomography apparatus includes an X-ray tube configured to emit X-rays, an X-ray detector configured to detect X-rays passing through a subject in order to acquire projection data, a processor configured to reconstruct tomographic image data on the basis of the projection data, and an interlock unit configured to monitor generation of an arc in the X-ray tube. When an arc in the X-ray tube is detected, the interlock unit stops emitting X-ray emission from the X-ray tube. When a predetermined period of time elapse from the stop of X-ray emission, the interlock unit restarts X-ray emission from the X-ray tube.

23 Claims, 7 Drawing Sheets

X-RAY COMPUTED TOMOGRAPHY APPARATUS

CROSS-REFERENCE TO RELATED APPLICATIONS

This application is based upon and claims the benefit of priority from the prior Japanese Patent Application No. 11-333370, filed Nov. 24, 1999, the entire contents of which are incorporated herein by reference.

BACKGROUND OF THE INVENTION

The present invention relates to an X-ray computed tomography apparatus having an interlock function of monitoring the operating state of an X-ray tube device and stopping all operations pertaining to scan, including the stop of X-ray emission, when something is wrong about the X-ray tube device.

Helical scan is a scan scheme of continuously and quickly acquiring projection data of a subject in a wide range by continuously rotating an X-ray tube and continuously moving a top plate.

Almost all X-ray computed tomography apparatuses have a function of monitoring an X-ray tube to assure the safety of a subject. The state of the X-ray tube is monitored from various viewpoints using various items such as a tube voltage, tube current, filament current, tube temperature, and cool pump operating status. If any one of the plurality of items exhibits an error value, all operations pertaining to projection data acquisition operation (scanning) are forcibly stopped. More specifically, tube voltage impression, filament current supply, cool pump driving, rotation of a ring on which the X-ray tube and detector are mounted, movement of the top plate of a bed are stopped. This function is called an interlock function.

When scan is stopped by this interlock function, an operator tries to find a cause of the stop of scan and performs a job to remove the cause, as needed. In some case, scan must be restarted from the beginning. In radiographic examination, for example, a change in CT value over time is one of the most important pieces of information. When scan is interrupted by the interlock function, the radiographic effect mostly disappears before the restart of radiographic examination. A contrast medium must be injected again to restart scan from the beginning. In helical scan described above, as the position of the subject often changes while scan is stopped, scan must be restarted from the beginning.

BRIEF SUMMARY OF THE INVENTION

It is an object of the present invention to reduce the frequency of the restart of scan in an X-ray computed tomography apparatus having an interlock function.

An X-ray computed tomography apparatus comprises an X-ray tube configured to emit an X-ray, an X-ray detector configured to detect an X-ray passing through a subject in order to acquire projection data, a processor configured to reconstruct tomographic image data on the basis of the projection data, and an interlock unit configured to monitor generation of an arc in the X-ray tube. When an arc in the X-ray tube is detected, the interlock unit stop X-ray emission from the X-ray tube. When a predetermined period of time elapse from the stop of X-ray emission, the interlock unit restarts X-ray emission from the X-ray tube.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Preferred embodiments of X-ray computed tomography apparatuses according to the present invention will be described in detail with reference to the accompanying drawing. Computed tomography apparatuses are classified into various types of apparatuses such as a rotate/rotate-type apparatus for integrally rotating an X-ray tube and X-ray detector around a subject and a stationary/rotate-type apparatus for rotating only an X-ray tube around a subject while a large number of detection elements are arranged in a ring. The present invention is applicable to any type and will be explained using the most popular rotate/rate-type apparatus as an example.

To reconstruct one tomographic image, a projection data set around the subject, i.e., through about 360° is generally required. Even in a half-scan method, a projection data set of 180°+α (α is the view angle) is required. The present invention is applicable to either scheme. The former method of reconstructing one tomographic image from the projection data set of about 360° is employed hereinafter.

First Embodiment

Figure 1:
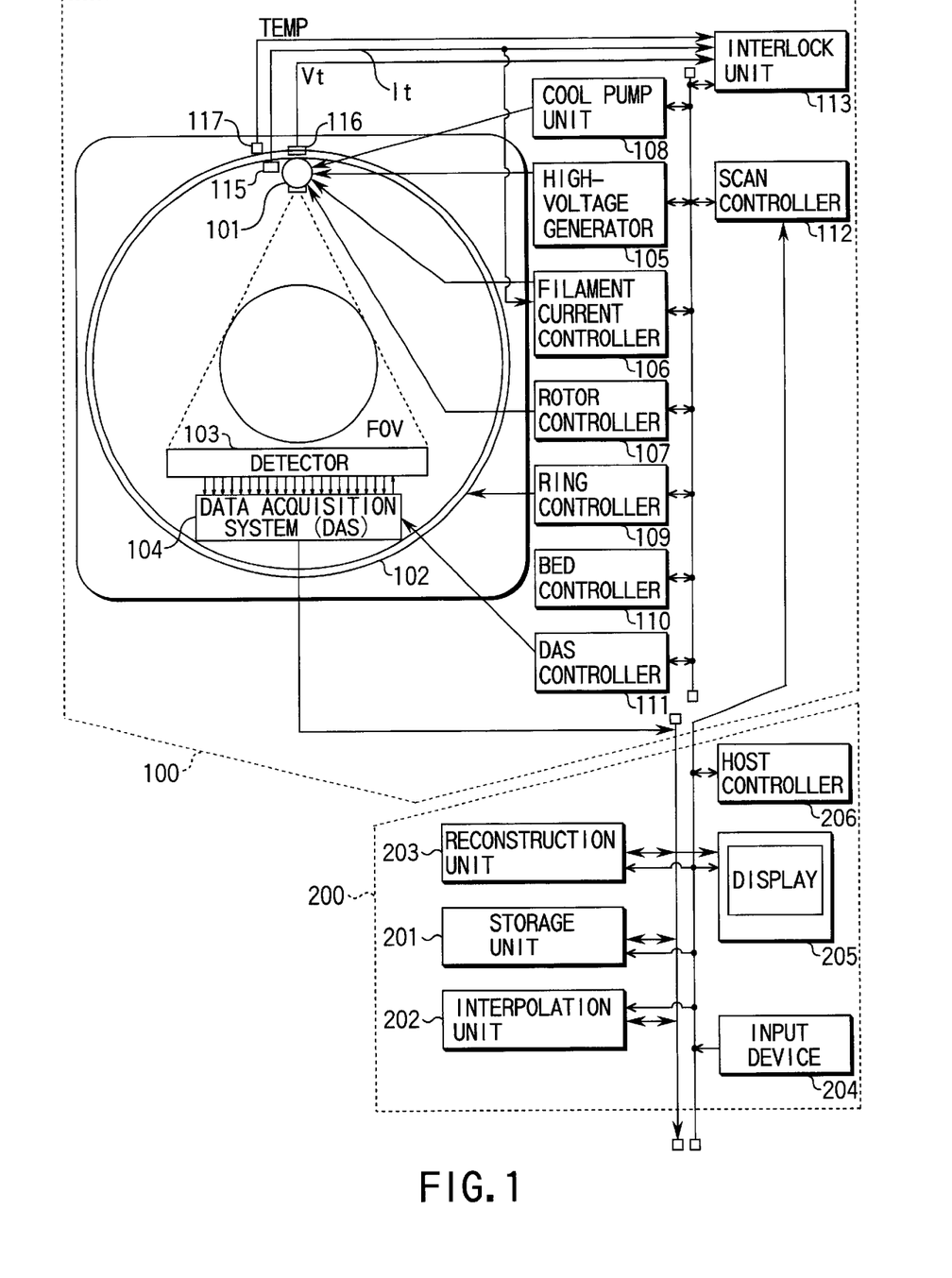
FIG. 1 is a view showing the arrangement of the main part of an X-ray computed tomography apparatus according to the first embodiment of the present invention.

FIG. 1 shows the arrangement of the main part of a computed tomography apparatus according to the first embodiment. This computed tomography apparatus is comprised of a gantry unit 100 and computer unit 200. The gantry 100 is made up of an X-ray tube 101 and a plurality of constituent components necessary for acquiring projection data. The X-ray tube 101 is mounted on a rotary ring 102. The X-ray tube 101 has a plurality of types of sensors necessary for monitoring various operating states, such as a voltmeter 115 for sensing a tube voltage, an ammeter 116 for sensing a tube current, and a temperature sensor 117 for sensing the internal temperature of the X-ray tube 101.

A multichannel type X-ray detector 103, data acquisition system 104, and the like are attached to the rotary ring 102 in addition to the X-ray tube 101. The X-ray detector 103 opposes the X-ray tube 101 through a photographic area. In projection data acquisition (scanning), a subject lying on a bed is located in the photographic area.

Projection data acquired by the data acquisition system 104 is temporarily stored in a storage unit 201 in the computer unit 200. In addition to the storage unit 201, the computer unit 200 is comprised of a host controller 206, an interpolation unit 202 for generating projection data (interpolated data), instead of projection data exhibiting an error value upon generation of an arc, on the basis of actually acquired projection data (real data), a reconstruction unit 203 for reconstructing tomographic image data on the basis of the real data of 360° or a combination of 360° real data and interpolated data, a display 205 for displaying the resultant tomographic image data, and an input device 204 having the function of allowing the operator to select an operation mode of an interlock unit 113 (to be described later).

As is known well, discharge is normal operation, while an arc generation is an error.

Referring back to FIG. 1, in addition to the X-ray tube and the like, the gantry unit 100 is comprised of a high-voltage generator 105 for impressing a tube voltage (high voltage) to the X-ray tube 101, a rotor controller 107 for rotating and driving the rotary anode of the X-ray tube 101, a cool pump unit 108 for cooling the X-ray tube 101, a ring controller 109 for rotating and driving the rotary ring 102, a bed controller 110 for moving the top plate of the bed, and a DAS controller 111 for controlling the operation of the data acquisition system 104.

The gantry unit 100 further comprises a filament current controller 106 for supplying a filament current to the X-ray tube 101. This filament current controller 106 has the feedback function of adjusting the filament current on the basis of the tube current sensed by the ammeter 116 in order to relatively stabilize the tube current to a predetermined value.

A scan controller 112 controls the high-voltage generator 105, filament current controller 106, rotor controller 107, cool pump unit 108, ring controller 109, bed controller 110, and DAS controller 111 to scan the subject.

The scan controller 112 is connected to the interlock unit 113. The interlock unit 112 receives a sensing signal from the voltmeter 115, a sensing signal from the ammeter 116, a sensing signal from the temperature sensor 117, and sensing signals from sensors arranged in the cool pump unit 108 to sense various operating states, e.g., the temperature and pressure of cooling oil.

The interlock unit 113 monitors the operating state of the X-ray tube 101 on the basis of these sensing signals from various viewpoints. When an error occurs in the X-ray tube 101, the interlock unit 113 outputs an interlock signal for emergency stop of scan to the scan controller 112. In addition to this original interlock function, the interlock unit 113 has the X-ray suspend function, as a characteristic feature, of outputting a suspend signal in place of the interlock signal to the scan controller 112 when the X-ray tube 101 is set in a specific state.

Upon receiving the interlock signal from the interlock unit 113, the scan controller 112 urgently stops all motions pertaining to scan operation for acquiring the projection data. More specifically, tube voltage impression from the high-voltage generator 105 to the X-ray tube 101 is stopped to stop emitting X-rays. Filament current supply from the filament current controller 106 to the X-ray tube 101 is stopped. The rotary anode and rotary ring 102 stop rotating, the top plate of the bed stops moving, and the DAS 104 stops data acquisition operation.

Upon receiving the suspend signal from the interlock unit 113, the scan controller 112 only stops impressing the tube voltage from the high-voltage generator 105 to the X-ray tube 101. The scan controller 112, however, outputs control signals to the high-voltage generator 105, filament current controller 106, ring controller 109, bed controller 110, cool pump unit 108, and DAS controller 111 so as not to stop, i.e., so as to continue all other operations pertaining to scan, i.e., filament current supply from the filament current controller 106 to the X-ray tube 101, rotation of the rotary anode and rotary ring 102, movement of the top plate of the bed, operation of the cool pump, and data acquisition operation of the DAS 104.

When a predetermined period of time, e.g., 100 ms, has elapsed from generation of the suspend signal, the interlock unit 113 stops generating the suspend signal. When the supply of the suspend signal is stopped, the scan controller 112 restarts impressing the tube voltage from the high-voltage generator 105 to the X-ray tube 101 and controls the high-voltage generator 105 to restart X-ray emission.

Of a plurality of operations pertaining to scan, operations except X-ray emission continue. When X-ray emission is restarted, normal scan can be immediately restarted.

The situation in which a suspend signal is generated, i.e., the specific state of the X-ray tube 101 is a state in which only an arc is generated. That is, any state other than that in which an arc is generated and overheat or the like occurs is normal. This arc is generated due to dust or fine particles in the X-ray tube 101 or a decrease in vacuum degree.

The above-mentioned arc generation is caused by dust, fine particles, or the decrease in vacuum degree, and is not an apparatus failure. No special repair is required, and the arc phenomenon often naturally disappears. To recover the normal state from the arc phenomenon earlier than natural disappearance, X-ray emission is stopped for a predetermined period of time (100 ms). When the predetermined period of time has elapsed upon generating the arc, X-ray emission is restarted. At the time of this restart, the arc phenomenon is often eliminated. If the arc is still being generated, all the operations pertaining to scan including X-ray emission are stopped. If the arc has disappeared, scan is continued.

The data acquired for the period in which X-rays are kept stopped are errors. The error data acquired in this period are replaced with interpolated data generated from the projection data (real data) actually acquired before and after the period.

Figure 2:
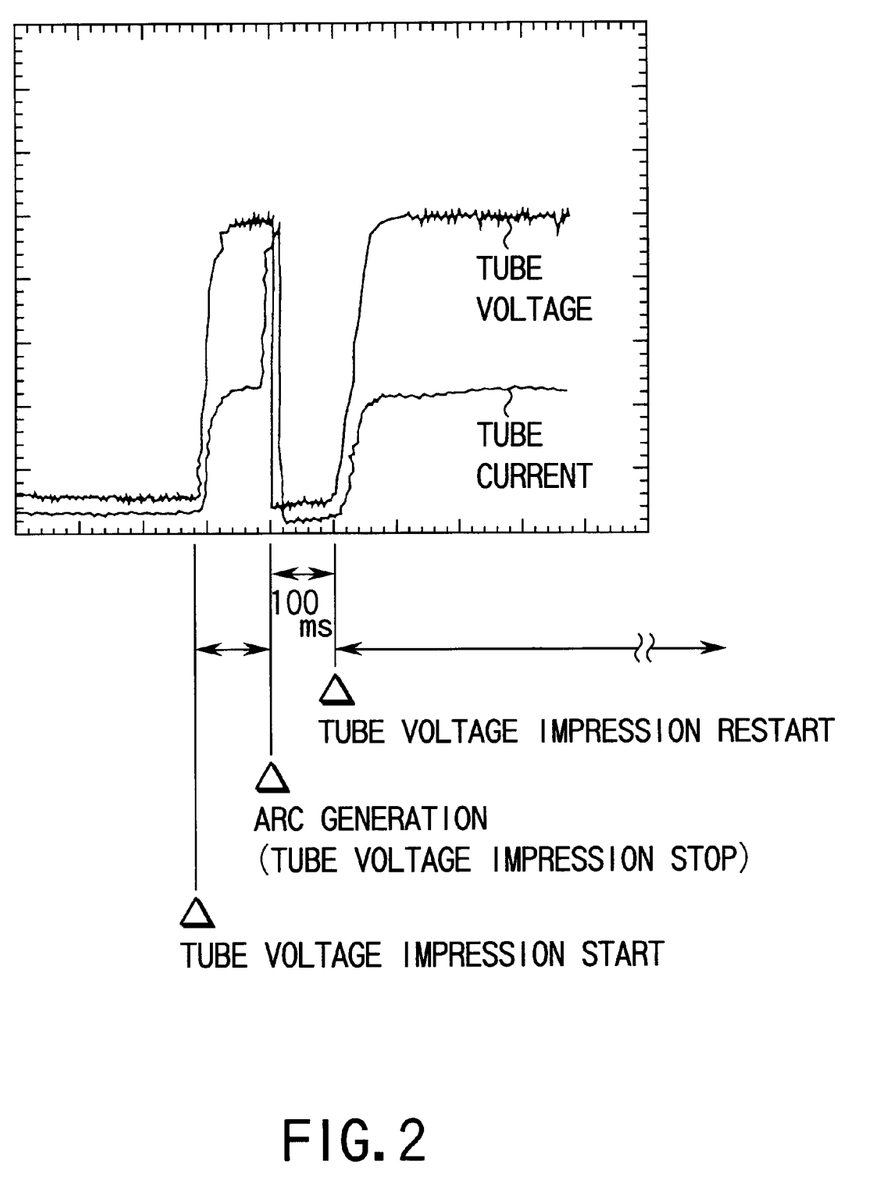
FIG. 2 is a timing chart showing operation of the first embodiment.

FIG. 2 shows changes in tube current and voltage as a function of time. When an arc is generated, the tube current abruptly increases while the tube voltage abruptly decreases. To determine arc generation with high precision, arc generation is determined when the following three conditions are satisfied:

(1) the tube current is larger than a first threshold value TH1;

(2) the tube voltage is lower than a second threshold value TH2; and (3) the descending gradient of the tube voltage is larger (steeper) than a threshold value.

When the operation error of the X-ray tube 101 is determined to be caused by only an arc on the basis of the above determination criteria, the interlock unit 113 generates a suspend signal. The high-voltage generator 105 stops impressing the tube voltage to the X-ray tube 101. However, filament current supply from the filament current controller 106 to the X-ray tube 101, rotation of the rotary anode and rotary ring 102, movement of the top plate of the bed, operation of the cool pump, and data acquisition operation of the DAS 104 continue without any stop.

When the predetermined period of time (100 ms) has elapsed from generation of the suspend signal, the interlock unit 113 stops generating the suspend signal. This makes it possible to restart X-ray emission and restore a scan enable state.

The actual time from the stop of impressing the tube voltage to the restart of impressing the tube voltage is not limited to 100 ms. The stop time should be set in consideration of an arc disappearance possibility and interpolation accuracy. That is, the longer the stop time, the higher the arc disappearance possibility and the lower the interpolation accuracy. In consideration of both the arc disappearance possibility and interpolation accuracy, the stop time is preferably 100 ms.

The interlock signal and suspend signal are also supplied to the host controller 206. In accordance with the interlock signal, the host controller 206 supplies to the display 205 a signal for displaying a message representing the stop of scan. A message displayed on the display 205 may represent an errored unit (e.g., an X-ray tube) or information (e.g., an arc) representing the cause of the error. Alternatively, the message representing the errored unit or information representing the cause of the error may be stored and so displayed as to allow a serviceman to confirm the message at the time of inspection or repair. A function of transferring to a business office or maker the message representing the errored unit or the information representing the cause of the error may be provided. This makes it possible for a serviceman to check and repair only the errored unit at the time of inspection and repair, thereby shortening the work time.

In accordance with the suspend signal, the host controller 206 supplies to the display 205 a signal for displaying a message representing the stop of X-ray emission.

The interlock unit 113 has the function of stopping scan as follows. When an arc is generated by the X-ray tube 101 at a relatively high frequency, for example, when an arc is generated three times in 10 sec, the interlock unit 113 determines a high possibility of an arc being generated due to an apparatus failure. When the third arc is detected, the interlock unit 113 generates an interlock signal in place of a suspend signal, thereby stopping scan of the subject.

As described above, according to this embodiment, when the X-ray tube generates an arc, only X-ray emission is stopped, and other operations pertaining to scan continue. When the predetermined period of time has elapsed, X-ray emission is automatically restarted. By this time, the arc phenomenon often disappears. Since the operations except X-ray emission have continued, the restart of X-ray generation allows the immediate restart of scan and the restart of acquiring projection data.

Although projection data acquisition operation continues during the X-ray stop period, data output from the detector 103 during this period are errors. For example, a slice position for reconstructing a tomographic image can be arbitrarily designated in helical scan. However, some of 360° projection data corresponding to the slice position are missing. The interpolation unit 201 must interpolate the missing projection data on the basis of the projection data actually acquired at a position near this slice position or a combination of the actually acquired projection data and their opposing data.

As a typical example of the interpolation method, missing data are calculated on the basis of the projection data (real data) acquired in the previous rotation and the projection data (real data) acquired in the next rotation while the angle (view) of the X-ray tube 101 remains the same. When the X-ray stop period is set relatively long, one of the projection data (real data) acquired in the previous rotation and the projection data (real data) acquired in the next rotation may be missing.

The interpolation unit 202 has the function of, when data to be used for interpolation is unfortunately missing, calculating the missing data using projection data (normal value) acquired for a period except the stop period of the tube voltage at a position closest to the missing data position. By this function, when scan is restarted, including the tube voltage impression stop and restart, projection data acquired between the stop and restart of tube voltage impression exhibit error values. When interpolation and reconstruction are performed using these error values, an artifact occurs in the reconstructed tomographic image. However, when the projection data exhibiting the error values are replaced with the projection data exhibiting normal values, and interpolation is performed, no artifact occurs.

Figure 3A:
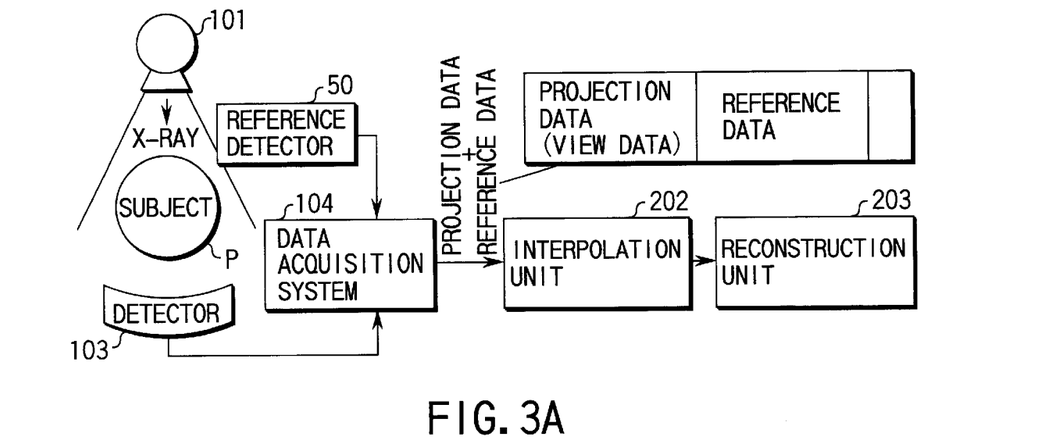
FIGS. 3A, 3B, and 3C are a view, graph, and block diagram, respectively, for explaining detection of the period of tube voltage impression stop in an interpolation unit in FIG. 1.
Figure 3B:
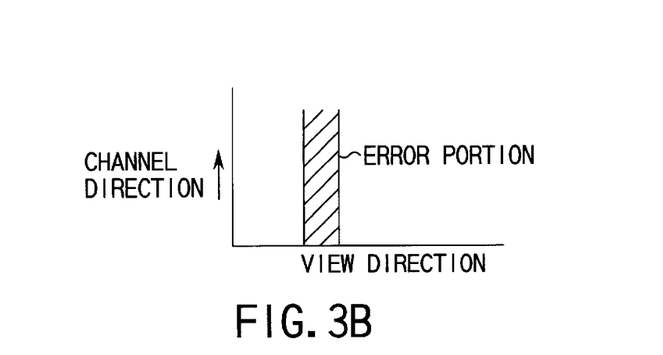
Figure 3C:
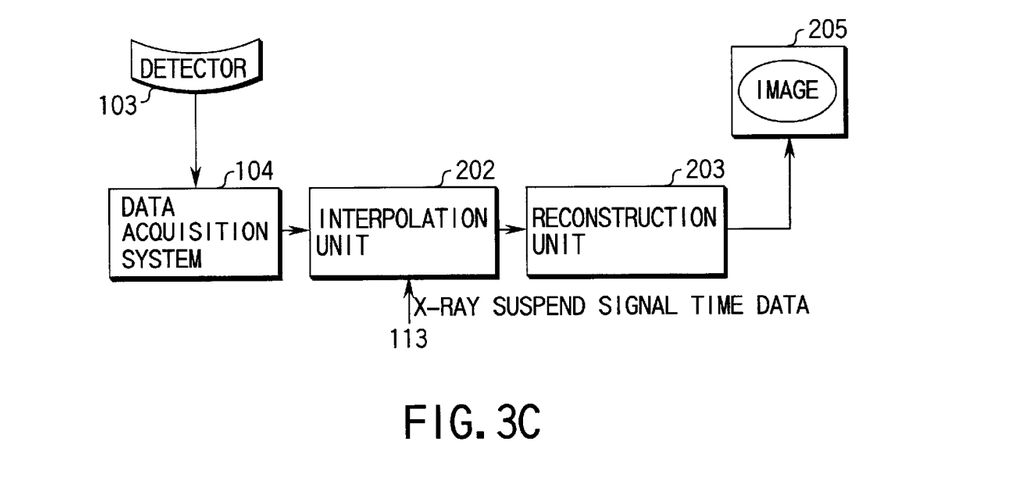

To prevent this artifact, the interpolation unit 202 must detect the stop period of the tube voltage. This detection method is not limited to any specific method. FIGS. 3A, 3B, and 3C show three variations of the detection method. In the method of FIG. 3A, one- or several-channel reference detector (X-ray detector) 50 is arranged between the X-ray tube 101 and the subject. Data (reference data) from the reference detector 50 is acquired by the data acquisition system 104 together with the projection data. The reference data exhibits almost zero level when no X-rays are emitted and a large value when X-rays are emitted. The interpolation unit 202 compares the value of the reference data with a threshold value. The interpolation unit 202 detects a period in which the value of the reference data is smaller than the threshold value, as the period from the tube voltage impression stop to the tube voltage impression restart. Alternatively, the projection data accompanying reference data smaller than the threshold value is detected as projection data exhibiting an error value acquired for the X-ray stop period.

Based on the same idea as described above, as shown in FIG. 3B, since no X-rays are emitted during the tube voltage stop period, the projection data value of the X-ray detector 101 exhibits almost zero. The data acquisition system 104 compares the acquired projection data with the threshold value to allow detection of the tube voltage stop period.

As shown in FIG. 3C, a time code (attached to the projection data) corresponding to the tube voltage impression stop and a time code corresponding to the tube voltage impression restart are received from the interlock unit 113. The period from the tube voltage impression stop to the tube voltage impression restart may be detected, or the projection data accompanying the reference data having a value smaller than the threshold value may be detected as projection data exhibiting an error value acquired during the tube voltage stop period.

Figure 4:
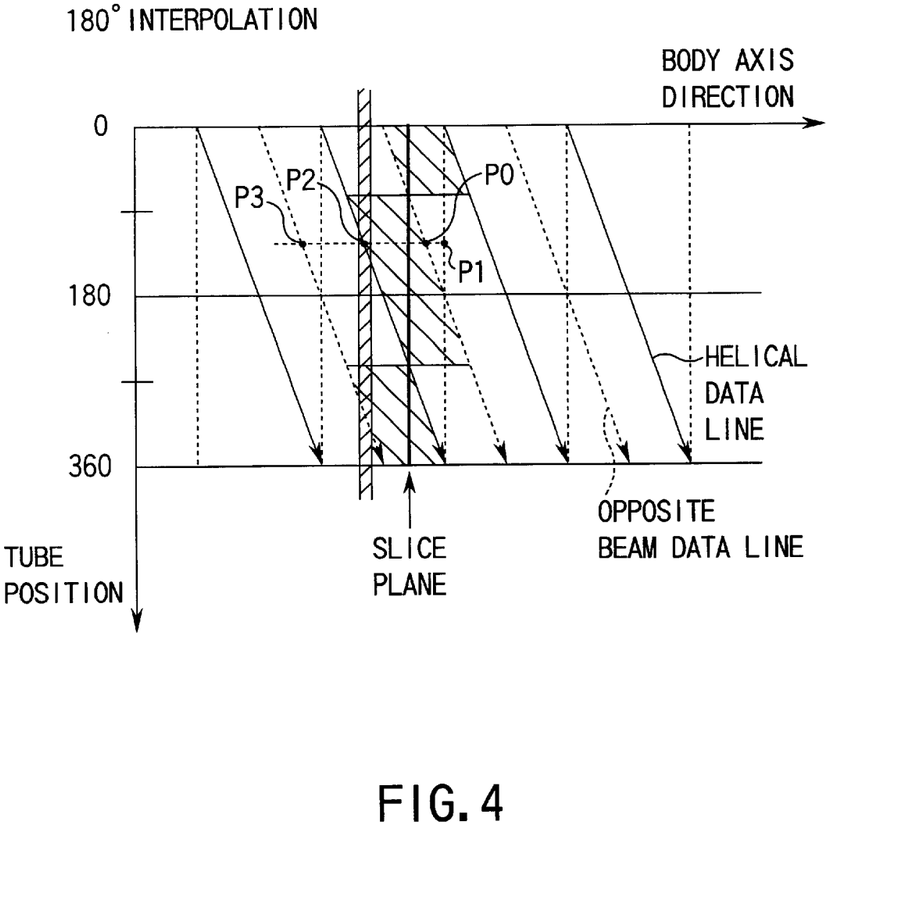
FIG. 4 is a view for explaining the interpolation method of the interpolation unit in FIG. 1.

In so-called 180° interpolation, i.e., interpolation for interpolating projection data of a designated slice on the basis of projection data actually acquired in the 180° range (hatched portion) centered on the designated slice and its opposing data (e.g., data on the same route in the opposite X-ray direction, and data obtained by interpolating data on a close route in the opposite X-ray direction), as shown in FIG. 4, projection data P0 at a given tube angle is interpolated from adjacent projection data P1 and P2. If the projection data P2 is projection data having an error value and acquired from the tube voltage impression stop to the tube voltage impression restart, the projection data P2 is replaced with projection data (opposing data in this case) P3 acquired at a position closest to the acquisition position of the projection data P2.

Figure 5A:
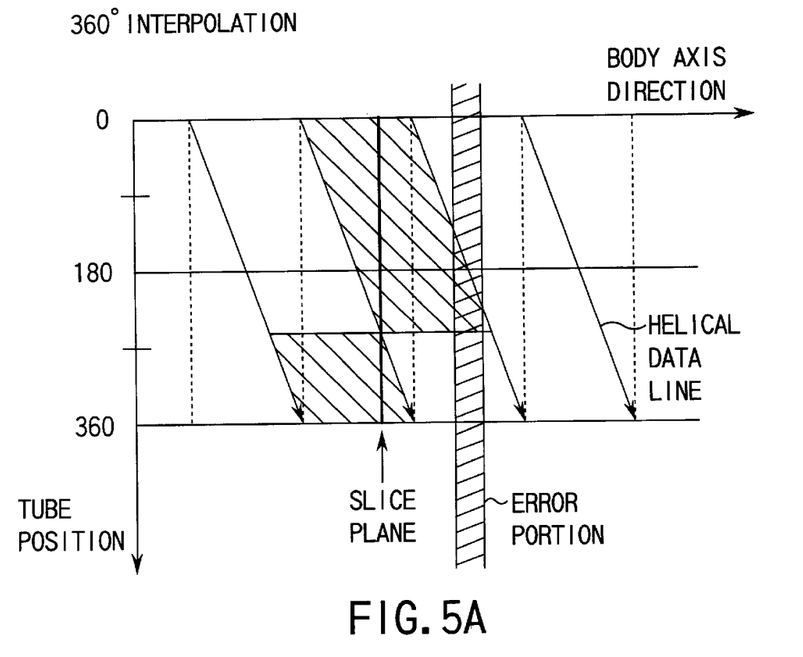
FIGS. 5A and 5B are views for explaining switching between the interpolation methods in the interpolation unit in FIG. 1.
Figure 5B:
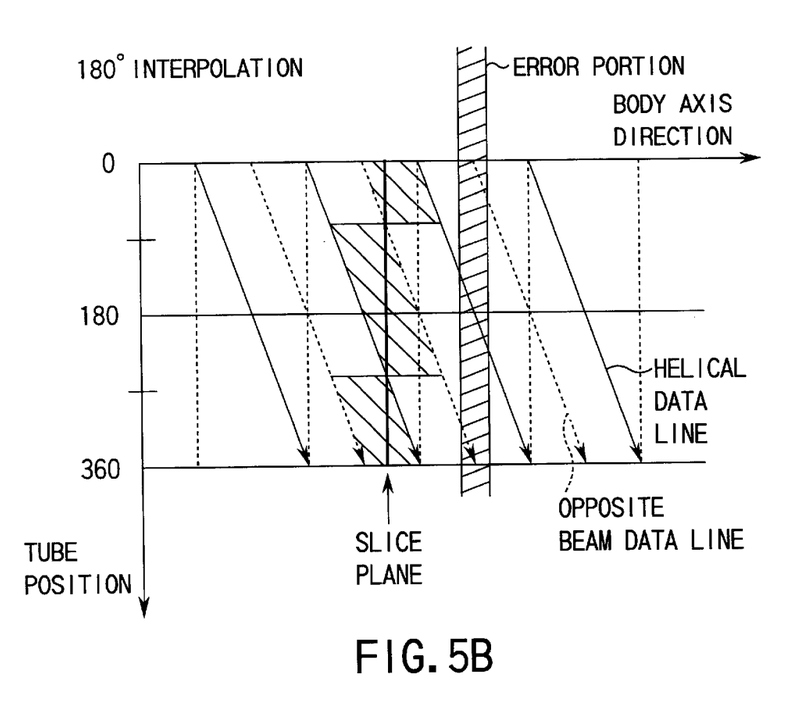

Interpolation may be performed using the following method as well. As shown in FIG. 5A, in place of using the opposing data, so-called 360° interpolation is used. The 360° interpolation performs interpolation using only the projection data actually acquired in the 360° range (hatched portion) centered on the designated slice. When the period from the tube voltage impression stop to the tube voltage impression restart partially overlaps the above range, the interpolation method is switched to the 180° interpolation method shown in FIG. 5B. The 180° interpolation method has a narrow range (range in the body axis direction) of data to be used for interpolation, i.e., about ½ the range of the 360° interpolation method. The possibility that the period from the tube voltage impression stop to the tube voltage impression restart partially overlaps the range is low. If the period from the tube voltage impression stop to the tube voltage impression restart partially overlaps the range of the 180° interpolation method, the projection data representing the error value and acquired for the period from the tube voltage impression stop to the tube voltage impression restart is replaced with the projection data acquired at a position closest to the acquisition position of the projection data having the error value, as shown in FIG. 4.

Note that the present invention is not limited to switching between the 360° and 180° interpolation methods, but can employ any interpolation method if an appropriate interpolation method can be selected from a variety of interpolation methods.

Figure 6A:
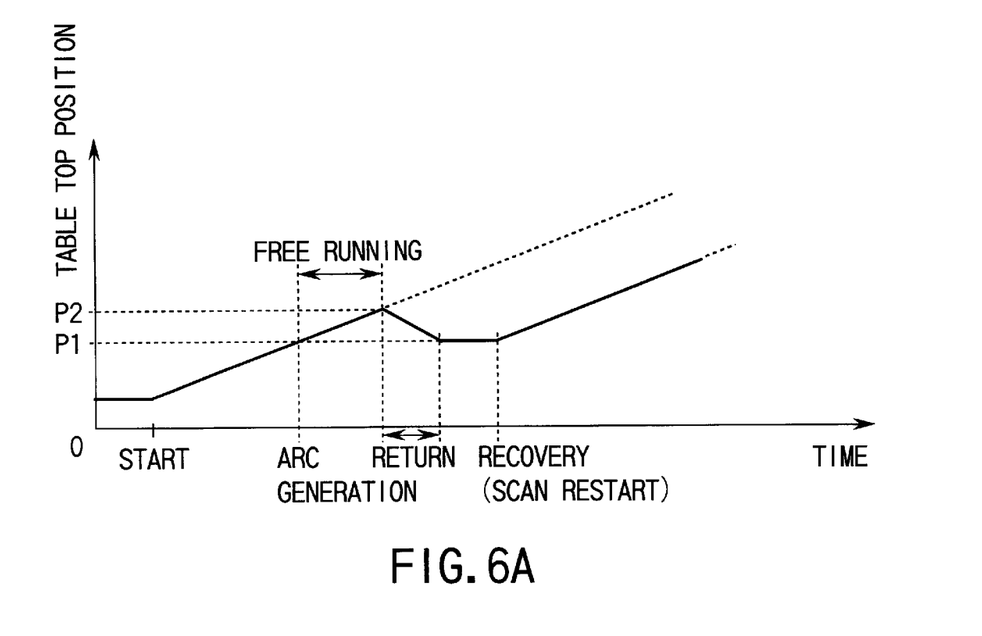
FIGS. 6A and 6B are views showing operation of returning the top plate of a bed under the control of a main controller in FIG. 1.

In the above description, the missing projection data during the X-ray stop period is interpolated. In helical scan, as shown in FIG. 6A, it is preferable that the top plate be returned from a position corresponding to the arc generation time by a total distance of the distance required for data interpolation and the approach distance of the top plate, and scan be restarted from the return position. In this case, missing of projection data does not occur, and no data interpolation is required.

Figure 6B:
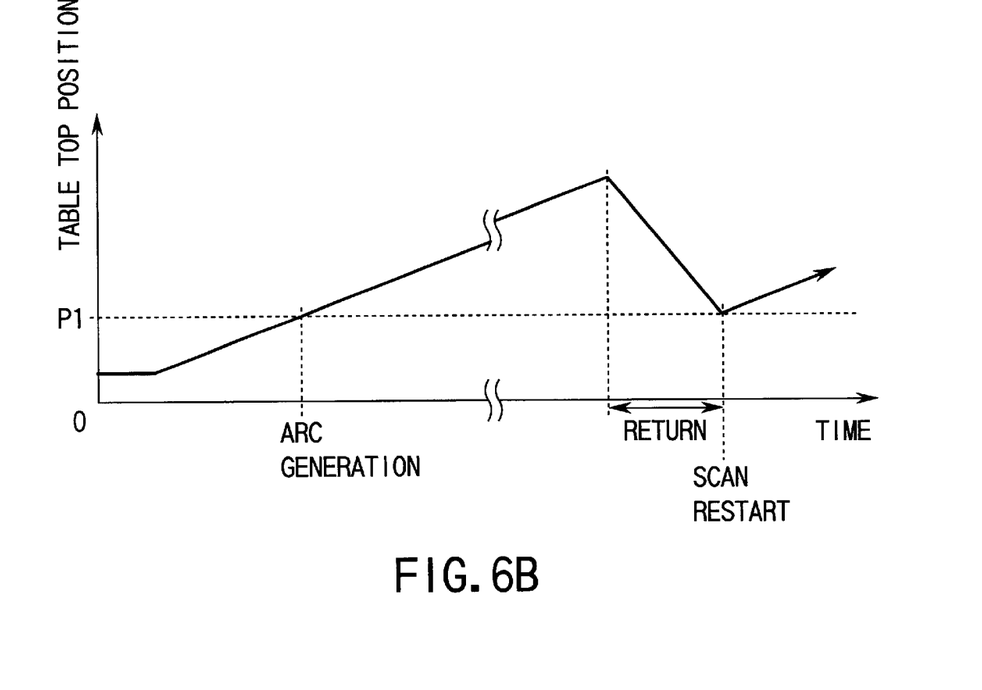

As shown in FIG. 6B, even if an arc is generated, scan may be continued to the end except the X-ray suspend period. Upon completion of the scan, the top plate may be returned from a position corresponding to the arc generation time by the total distance of the distance required for data interpolation and the approach distance of the top plate, and scan in the range corresponding to the X-ray suspend period may be restarted from the return position.

The ON/OFF mode of the method in FIG. 6A can be selected by an operator's instruction. Similarly, the ON/OFF mode of the method in FIG. 6B can be selected by an operator's instruction.

The ON/OFF mode of the X-ray suspend function described above can be selected by an operator's instruction.

As described above, according to this embodiment, it is highly probable that an arc generation as an abnormal phenomenon which abruptly increases the tube current and abruptly decreases the tube voltage as the main cause of vacuum degree degradation in the X-ray tube be naturally recovered. In such case, when impression of the tube current is restarted, often the abnormal phenomenon is naturally recovered and scan can be continued. Even if the interlock function is effected in helical scan or contrast examination, scan may not be restarted from the beginning.

Second Embodiment

The arrangement of an X-ray computed tomography apparatus according to the second embodiment is the same as that in FIG. 1, except a control mechanism of an interlock unit 113 and scan controller 112 upon generating an arc. The difference will be described below.

Figure 7:
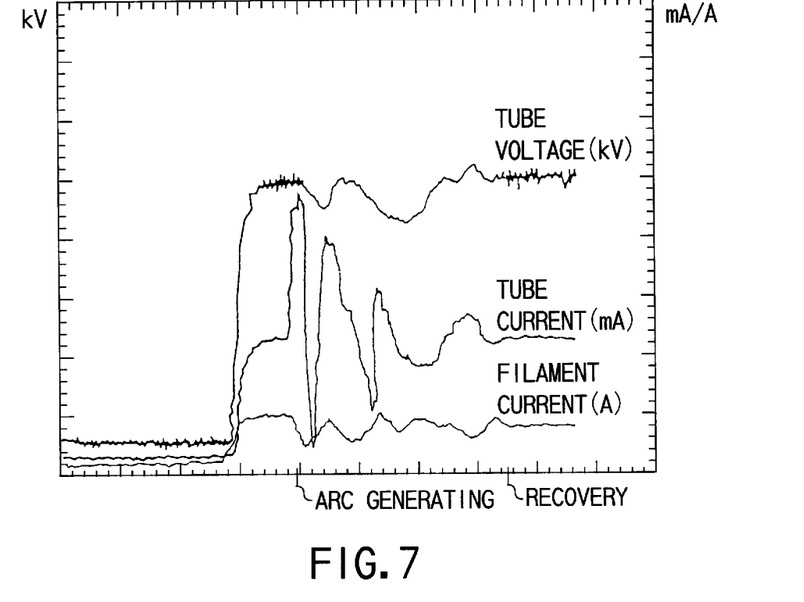
FIG. 7 is a timing chart showing operation of the second embodiment.

FIG. 7 shows a tube voltage curve, tube current curve, and filament current curve as a function of time under the control mechanism of the second embodiment. Most causes of arc generation are dust, fine particles, and degradation of the vacuum degree, but are not an apparatus failure. The arc phenomenon may often be naturally eliminated with a lapse of time.

This embodiment waits for natural recovery.

In the conventional monitoring function, when an arc is generated, the interlock function is effected to stop all operations pertaining to scan including X-ray emission. To the contrary, in this embodiment, even if an arc is detected, all operations pertaining to scan including X-ray emission continue. The operations include conventional feedback control for monitoring the tube current and adjusting the filament current in accordance with the monitoring result in order to stabilize the tube current.

The interlock unit 113 monitors the tube current, and when an arc is generated, generates a suspend signal. When the arc disappears, the interlock unit 113 stops outputting the suspend signal. Arc generation can be detected by an abrupt increase in tube current. Arc disappearance can be detected when variations in tube current converge to less than a predetermined value.

The interlock unit 113 keeps generating the suspend signal for a period from arc generation to arc disappearance. Unlike in the first embodiment, the scan controller 112 continues all operations pertaining to scan including X-ray emission even if the controller 112 receives a suspend signal from the interlock unit 113. The scan controller 112 transfers the suspend signal from the interlock unit 113 to a host computer 206.

The host computer 206 detects as an arc generating period a given period in which it receives the suspend signal. The host computer 206 instructs an interpolation unit 202 to interpolate the projection data of the given period using the projection data (real data) actually acquired during a period before or after the given period. The host computer 206 also instructs a reconstruction unit 203 to reconstruct a tomographic image using the resultant interpolated data and the real data.

In this embodiment, even if an arc is generated, scan continues. The data acquired for a period elapsed until the arc naturally disappears are not used. By this operation, even if an arc is generated, the frequency of restarting scan can be reduced.

Third Embodiment

The arrangement of an X-ray computed tomography apparatus according to the third embodiment is the same as that in FIG. 1, except the control mechanism of an interlock unit 113 and scan controller 112 upon generating an arc. The difference will be described below.

Figure 8:
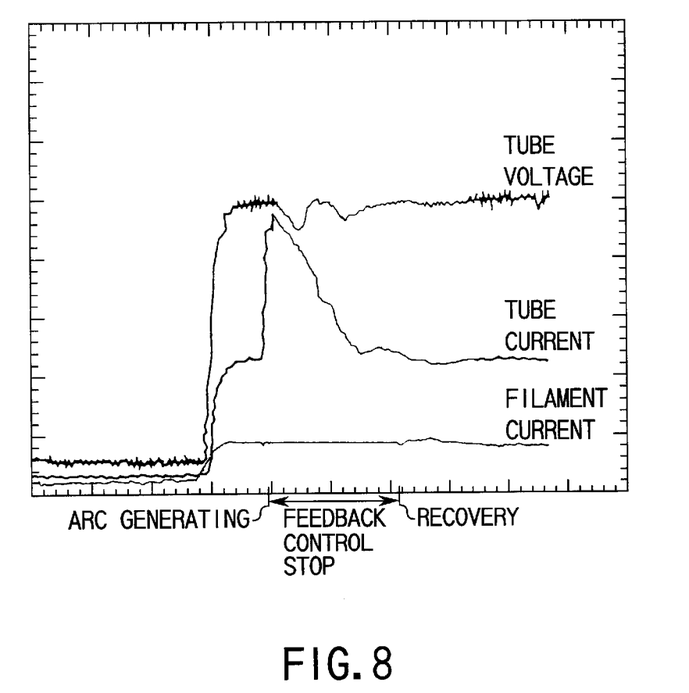
FIG. 8 is a timing chart showing operation of the third embodiment.

FIG. 8 shows a tube voltage curve, tube current curve, and filament current curve as a function of time under the control mechanism of the second embodiment. The second embodiment utilizes natural disappearance of the arc phenomenon. The third embodiment employs an implementation for positively eliminating the arc phenomenon.

As described above, according to the conventional monitoring function, when an arc is generated, the interlock function is effected to stop all operations pertaining to scan including X-ray emission. To the contrary, according to the third embodiment, when arc generation is detected, of all the operations pertaining to scan including X-ray emission, only feedback control for monitoring the tube current and adjusting the filament current in accordance with the tube current value in order to stabilize the tube current is stopped.

The interlock unit 113 monitors the tube current and when an arc is generated, generates a suspend signal. When the arc disappears, the interlock unit 113 stops outputting the suspend signal. Unlike in the second embodiment, upon receiving the suspend signal from the interlock unit 113, the scan controller 112 continues all operations pertaining to scan including X-ray emission except the feedback control for stabilizing the tube current. That is, upon receiving the suspend signal, the scan controller 112 outputs a control signal for stopping feedback control to a filament current controller 106 and outputs no control signals to other constituent components pertaining to scan.

Although all the scan operations including the feedback function continue in the arc generation period as in the normal period in the second embodiment, only the feedback function is stopped and other scanning operations continue in the third embodiment.

The feedback function is the function of decreasing the filament current when the tube current becomes larger than a predetermined value and increasing it when the tube current becomes smaller than the predetermined value, thereby stabilizing the tube current.

By this function, when the tube current abruptly increases due to an arc, the filament current is abruptly decreased to decrease the tube current. The tube current abruptly decreases. When the tube current abruptly decreases, the filament current abruptly increases to abruptly increase the tube current. The tube current abruptly increases.

As described above, the feedback function is effective in normal operation, but may cause instability of the tube current in an abnormality such as arc generation. That is, the feedback function may prolong the period from the time when the tube current becomes unstable due to arc generation to the time when the arc disappears and the tube current returns to a relatively stable state.

According to this embodiment, the feedback function is stopped in synchronism with arc generation. The feedback function is restarted after the tube current recovers a relatively stable state. The period from the time when the tube current becomes unstable due to arc generation to the time when the arc disappears and the tube current returns to a relatively stable state can be shortened.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus comprising:
   an X-ray tube configured to emit an X-ray;
   an X-ray detector configured to detect an X-ray passing through a subject in order to acquire projection data;
   a processor configured to reconstruct tomographic image data on the basis of the projection data; and
   an interlock unit configured to monitor generation of an arc in said X-ray tube, when the arc is detected, stop X-ray emission from said X-ray tube, and when a predetermined period of time elapse from the stop of X-ray emission, restarts X-ray emission from said X-ray tube.

2. An apparatus according to claim 1, wherein the arc decreases a dose of X-ray to be lower than a predetermined value.

3. An apparatus according to claim 1, wherein at least one of rotation operation of a rotor of a rotary anode of said X-ray tube and operation of supplying a filament current to said X-ray tube continues even for an X-ray stop period.

4. An apparatus according to claim 1, wherein rotation operation of at least one of said X-ray tube and said X-ray detector around the subject continues for an X-ray stop period as in an X-ray emission period.

5. An apparatus according to claim 1, wherein said interlock unit inhibits restart of generating the X-ray when a frequency of generating the arc exceeds a predetermined value.

6. An apparatus according to claim 1, wherein said interlock unit is operative selectively in a first mode for stopping/restarting the X-ray and a second mode for stopping scan operations including the stop of the X-ray when the arc of said X-ray tube is detected.

7. An apparatus according to claim 1, further comprising an interpolation unit configured to interpolate projection data corresponding to an X-ray stop period on the basis of projection data acquired for an X-ray emission period.

8. An apparatus according to claim 7, wherein said interpolation unit interpolates the projection data corresponding to the X-ray stop period on the basis of the projection data acquired for the X-ray emission period and opposing data thereof.

9. An apparatus according to claim 7, wherein said interpolation unit has a plurality of types of interpolation techniques selectively used by a user instruction.

10. An apparatus according to claim 9, wherein the plurality of types of interpolation techniques include a 180° interpolation technique and a 360° interpolation technique.

11. An apparatus according to claim 1, further. comprising a display unit configured to display information pertaining to the arc.

12. An apparatus according to claim 1, further comprising a storage unit configured to store information pertaining to the arc and a display unit configured to display the stored information pertaining to the arc.

13. An apparatus according to claim 1, further comprising a storage unit configured to store information pertaining to the arc and a transfer unit configured to transfer the stored information pertaining to the arc to an external device.

14. An apparatus according to claim 1, further comprising a controller configured to return positions of said X-ray tube and said X-ray detector relative to the subject to positions before the arc is generated, after an arc of said X-ray tube is detected.

15. An apparatus according to claim 1, further comprising a controller configured to return positions of said X-ray tube and said X-ray detector relative to the subject to positions before the arc is generated, after an arc. of said X-ray tube is detected and scan is complete.

16. An apparatus according to claim 1, further comprising a controller configured to return positions of said X-ray tube and said X-ray detector relative to the subject to positions before the arc is generated, after an arc of said X-ray tube is detected and before generation of the X-rays is restarted.

17. An apparatus according to claim 1, further comprising a gantry including said X-ray tube and said X-ray detector, a bed on which the subject lies down, and a controller for controlling said gantry and said bed for helical scan, said controller for returning positions of said gantry and bed relative to each other to positions before the arc is generated by a total distance of a distance required for data interpolation and an approach distance.

18. An apparatus according to claim 1, further comprising a gantry including said X-ray tube and said X-ray detector, a bed on which the subject lies down, and a controller for controlling at least one of said gantry and said bed to intermittently change the positions of said gantry and said bed relative to each other, said controller for returning positions of said gantry and said bed relative to each other to positions whe[008e] the arc is generated.

19. An X-ray computed tomography apparatus comprising:

an X-ray tube configured to emit an X-ray;

an X-ray detector configured to detect an X-ray passing through a subject in order to acquire projection data;

a processor configured to reconstruct tomographic image data on the basis of the projection data;

a feedback unit configured to execute feedback operation for adjusting a filament current in accordance with a tube current of said X-ray tube; and an interlock unit configured to monitor an operating state of said X-ray tube, and when an operation error occurs in said X-ray tube, stop scan operations including X-ray emission from said X-ray tube and the feedback operation, wherein when the operation error of said X-ray tube is caused by an arc, said interlock unit does not stop the scan operations in order to continue the scan operations including X-ray emission from said X-ray tube and the feedback operation.

20. An X-ray computed tomography apparatus comprising:

an X-ray tube configured to emit an X-ray;

an X-ray detector configured to detect an X-ray passing through a subject in order to acquire projection data;

a processor configured to reconstruct tomographic image data on the basis of the projection data;

a feedback unit configured to execute feedback operation for adjusting a filament current in accordance with a tube current of said X-ray tube; and an interlock unit configured to monitor an operating state of said X-ray tube, and when an operation error occurs in said X-ray tube, stop scan operations including X-ray emission from said X-ray tube and the feedback operation, wherein when the operation error of said X-ray tube is caused by an arc, said interlock unit stop the feedback operation and continuing scan operations including the X-ray emission from said X-ray tube and excluding the feedback operation.

21. An X-ray computed tomography apparatus comprising:

a scan unit configured to execute scan operation for acquiring projection data pertaining to a subject using an X-ray;

a reconstruction unit configured to reconstruct tomographic image data on the basis of the projection data;

a detection unit configured to detect an error of the scan operation; and an interlock unit configured to stop the scan operation when an error of the scan operation is detected, wherein said interlock unit continues all or some of the scan operations when the error of the scan operations is caused by an arc.

22. An X-ray computed tomography apparatus comprising:

an X-ray tube configured to generate an X-ray;

an X-ray detector configured to detect an X-ray passing through the subject in order to acquire projection data;

a reconstruction unit configured to reconstruct tomographic image data on the basis of the projection data;

a detection unit configured to detect an operating state of said X-ray tube; and an interlock unit configured to stop X-ray emission from said X-ray tube when an error occurs in said X-ray tube, and when the error of said X-ray tube is caused by an arc, recover a tube voltage and/or tube current of said X-ray tube to a predetermined value.

23. An X-ray computed tomography apparatus comprising:

a gantry configured to acquire projection data, said gantry having an X-ray tube for generating an X-ray and an X-ray detector for detecting an X-ray passing through a subject;

a bed configured to hold the subject between said X-ray tube and said X-ray detector;

a reconstruction unit configured to reconstruct tomographic image data on the basis of the projection data; and a controller configured to monitor generation of an arc in said X-ray tube and return, when an arc of said X-ray tube is detected, positions of said gantry and subject relative to each other to positions before the arc is generated.

* * * * *